US010480909B1

(12) United States Patent
Brown (10) Patent No.: US 10,480,909 B1
(45) Date of Patent: Nov. 19, 2019

(54) PRISONER CONTROL DEVICE, SYSTEM, AND METHOD

(71) Applicant: LEEB Innovations, LLC, West Warwick, RI (US)

(72) Inventor: Leveland Brown, West Warwick, RI (US)

(73) Assignee: LEEB Innovations, LLC, West Warwick, RI (US)

( * ) Notice: Subject to any disclaimer, the term of this patent is extended or adjusted under 35 U.S.C. 154(b) by 0 days.

(21) Appl. No.: 16/235,944

(22) Filed: Dec. 28, 2018

(51) Int. Cl.
| F41H 13/00 | (2006.01) |
| G01S 19/01 | (2010.01) |
| E05B 75/00 | (2006.01) |
| H05C 1/04 | (2006.01) |

(52) U.S. Cl.
CPC ......... *F41H 13/0018* (2013.01); *E05B 75/00* (2013.01); *G01S 19/01* (2013.01); *H05C 1/04* (2013.01)

(58) Field of Classification Search
CPC ...... F41H 13/0018; E05B 75/00; G01S 19/01; H05C 1/04
USPC .......................................................... 361/232
See application file for complete search history.

(56) References Cited

U.S. PATENT DOCUMENTS

| 6,072,396 | A  | 6/2000  | Gaukel          |
| 6,510,380 | B1 | 1/2003  | Curatolo et al. |
| 6,800,070 | B2 | 10/2004 | Mazidji et al.  |
| 6,933,851 | B2 | 8/2005  | Hahne et al.    |
| 6,999,295 | B2 | 2/2006  | Watkins, III et al. |
| 7,102,870 | B2 | 9/2006  | Nerheim         |
| 7,145,762 | B2 | 12/2006 | Nerheim         |
| 7,570,476 | B2 | 8/2009  | Nerheim         |
| 7,580,237 | B2 | 8/2009  | Nerheim         |
| 7,586,732 | B2 | 9/2009  | Myers           |
| 7,586,733 | B2 | 9/2009  | Nerheim         |
| 7,602,598 | B2 | 10/2009 | Nerheim         |
| 7,782,592 | B2 | 8/2010  | Nerheim         |
| 7,800,885 | B2 | 9/2010  | Brundula et al. |
| 7,916,446 | B2 | 3/2011  | Nerheim         |
| 8,321,124 | B2 | 11/2012 | Curatolo et al. |

(Continued)

FOREIGN PATENT DOCUMENTS

| EP | 17188150.1 A1 | 3/2019 |
| WO | 2008018728 A1 | 2/2008 |

(Continued)

*Primary Examiner* — Kevin J Comber
(74) *Attorney, Agent, or Firm* — Schneider IP Law LLC; Laura A. Schneider (57) ABSTRACT

A system for controlling prisoners and protecting security personnel or victims of domestic violence is disclosed. The system includes a first wearable device configured to be secured about an appendage of a person, and includes a GPS receiver module, an electroshock module and wireless receiver. A second wearable device is configured to be worn about an appendage of a person, and includes a GPS receiver module, a transmitter and activation switch. If the first wearable device is within a predefined radius of a second wearable device, activation of the activation switch causes the transmitter to send a signal to the receiver to activate the electroshock module. Additionally, the system may include a server that can selectively activate the electroshock module and display the location of the wearable devices on a map or floorplan.

20 Claims, 5 Drawing Sheets

(56) References Cited

U.S. PATENT DOCUMENTS

| | | |
|---|---|---|
| 8,514,070 B2 | 8/2013 | Roper et al. |
| 8,862,378 B2 | 10/2014 | Curatolo et al. |
| 8,879,232 B2 | 11/2014 | Ziriax et al. |
| 9,111,433 B2 | 8/2015 | Curatolo et al. |
| 9,386,438 B2 | 7/2016 | Hymowitz |
| 10,007,962 B2 | 6/2018 | Brans |
| 2004/0092874 A1 | 5/2004 | Mazidji et al. |
| 2006/0092028 A1 | 5/2006 | Lerch et al. |
| 2006/0244613 A1 | 11/2006 | Myers |
| 2008/0057976 A1 | 3/2008 | Rae et al. |
| 2011/0248853 A1 | 10/2011 | Roper et al. |
| 2012/0298119 A1* | 11/2012 | Reese .................. E05B 75/00 128/875 |
| 2013/0260785 A1* | 10/2013 | Shakespeare ........ H04W 64/00 455/456.1 |
| 2014/0159905 A1 | 6/2014 | Thompson |
| 2014/0194084 A1* | 7/2014 | Noonan ............... H04W 4/029 455/404.1 |
| 2017/0039833 A1 | 2/2017 | Baczuk et al. |
| 2017/0120932 A1 | 5/2017 | Szczerba et al. |
| 2017/0202180 A1 | 7/2017 | Yang |
| 2017/0221166 A1 | 8/2017 | Brans |
| 2018/0020786 A1 | 1/2018 | Fernandes Demetrio et al. |
| 2018/0178757 A1 | 6/2018 | Fernandes Demetrio |

FOREIGN PATENT DOCUMENTS

| | | | |
|---|---|---|---|
| WO | 2017050778 | A1 | 3/2017 |
| WO | 2019048580 | A1 | 3/2019 |

* cited by examiner

PRISONER CONTROL DEVICE, SYSTEM, AND METHOD

TECHNICAL FIELD

The present patent document relates generally to control systems for management and control of persons in protective custody, such as prisoner, or those with restraining orders in effect, and more particularly to a prisoner control system and method with improved protection of security personal and victims of domestic violence against attack.

BACKGROUND

Prior art system for tracking those on house arrest are known in the art. Such system include an ankle or wrist module with a global positioning system ("GPS") receiver and transmitter, to allow authorities to locate the wearer of the module. Such systems have limited use in a prison setting or for use to protect victims of domestic violence from an attack by the wearer of the module.

SUMMARY

Accordingly, there is a perceived need in the art for a prisoner tracking and control system that permits authorities and/or victims of domestic violence to halt an attack in progress or prevent an attack from occurring.

The prisoner control system and method described herein solves the problems of the prior art by providing a system for controlling prisoners using uniquely configured wearable devices. The system includes a first wearable device configured to be secured about an appendage of a person, and includes a GPS receiver module, an electroshock module and wireless receiver. A second wearable device is configured to be worn about an appendage of a person, and includes a GPS receiver module, a transmitter and activation switch. If the first wearable device is within a predefined radius of a second wearable device, activation of the activation switch causes the transmitter to send a signal to the receiver to activate the electroshock module. Additionally, the system may include a server that can selectively activate the electroshock module and display the location of the wearable devices on a map or floorplan.

A user wearing the second wearable device may activate an electroshock module on a subject wearing the first wearable device if the subject approaches within a predefined radius of the wearer. In this manner, user's that are security personnel or victim's of domestic violence may protect themselves against subjects that are prisoners and/or subject to restraining orders.

BRIEF DESCRIPTION OF THE DRAWINGS

Various aspects of at least one embodiment are discussed below with reference to the accompanying figures, which are not necessarily drawn to scale, emphasis instead being placed upon illustrating the principles disclosed herein. The figures are included to provide an illustration and a further understanding of the various aspects and embodiments, and are incorporated in and constitute a part of this specification, but are not intended as a definition of the limits of any particular embodiment. The figures, together with the remainder of the specification, serve only to explain principles and operations of the described and claimed aspects and embodiments, but are not to be construed as limiting embodiments. In the figures, each identical or nearly identical component that is illustrated in various figures is represented by a like numeral. For purposes of clarity, not every component may be labeled in every figure.

DETAILED DESCRIPTION OF THE ILLUSTRATIVE EMBODIMENTS

The examples of the methods and systems discussed herein are not limited in application to the details of construction and the arrangement of components set forth in the following description or illustrated in the accompanying drawings. It will be understood to one of skill in the art that the methods and systems are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

As will be described in greater detail below, in some embodiments, the system for controlling prisoners includes a first wearable device, worn by a prisoner, and a second wearable device, worn by a security guard or a protected person, such as a victim of domestic violence. The first wearable device is configured to be secured about an appendage of a person, and including a GPS receiver module, an electroshock module and wireless receiver. The second wearable devices configured and arranged to be worn about an appendage of a person, and includes a GPS receiver module, a transmitter and activation switch. If the first wearable device is within a predefined radius of the second wearable device, activation of the activation switch causes the transmitter to send a signal to the receiver to activate the electroshock module on the first wearable device, giving a stunning shock to the subject, thereby deterring the subject from approaching the person wearing the first wearable device.

In other embodiments, the system may further include a server configured to receive a GPS location from the first and second wearable devices and indicate the locations of the first and second wearable device on a map or floorplan. Furthermore, the electroshock module of the first wearable device may be selectively activated by a user through the server, or automatically, such as through a predetermined entering a predetermined radius of the second wearable device.

In yet other embodiments, the system the server may be configured to receive a GPS location from the first and second wearable devices and calculate a distance between the first and second wearable device. The server may be further configured to transmit a signal to the first wearable device to activate the electroshock module of the first wearable device if the first wearable device is within a predefined radius of the second wearable device. The activation may occur automatically or selectively, such as depressing of an activation switch.

Figure 1A:
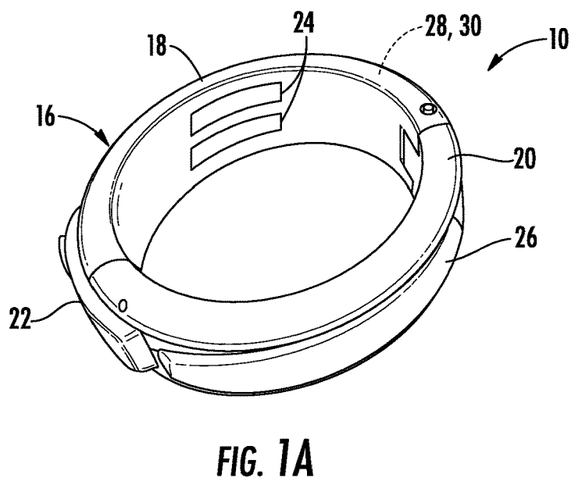
FIG. 1A is a bracelet according to the system and method described herein in a closed or locked position.
Figure 1B:
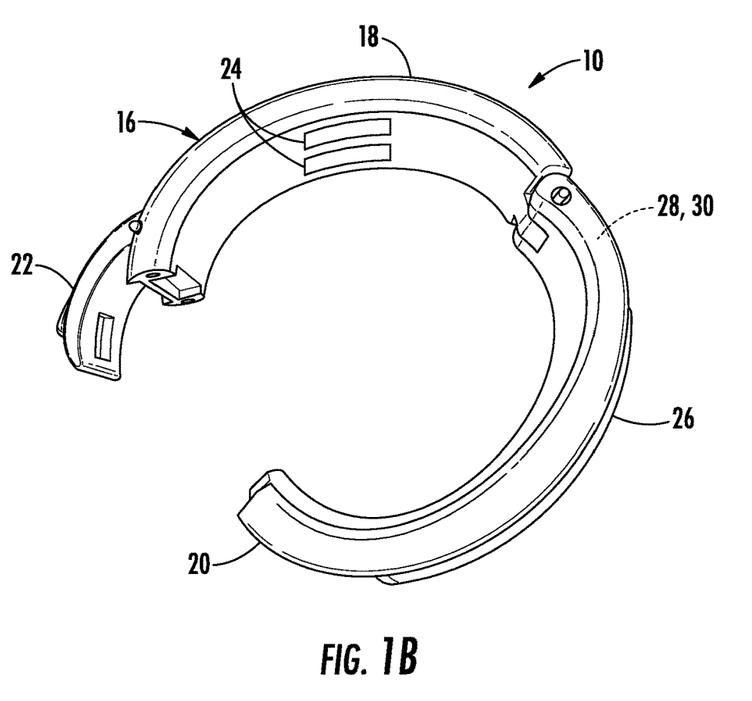
FIG. 1B is a perspective view of an embodiment of a bracelet according to the system and method described herein in an open or unlocked position.

Referring to FIGS. 1A and 1B, an embodiment of a wearable device as described herein is generally illustrated at 10. The wearable device 10 may come in two general configurations, a first configuration for wear by a subject 12, such as a prisoner, a person under protective custody, a person under house arrest, or a person subject to a restraining order, and a second configuration for wear by a user 14, such as a security guard, policeman, or victim of domestic violence or other person under the protection of a restraining order. The wearable device 10 may be configured as a lockable cuff or bracelet having body 16 with a first section 18 and a hinged second section 20. The body 16 includes a dual locking system 22 to lock the first section 18 and second section 20 in place on a wrist or ankle of a subject 12.

In some embodiments the first section 18 of the wearable device includes a pair of electrodes 24 for the electroshock module. Alternatively, the electrodes 24 may protrude from the second section 20 or on another portion of an inner surface of the body 16, contacting the wearer's skin.

Figure 2A:
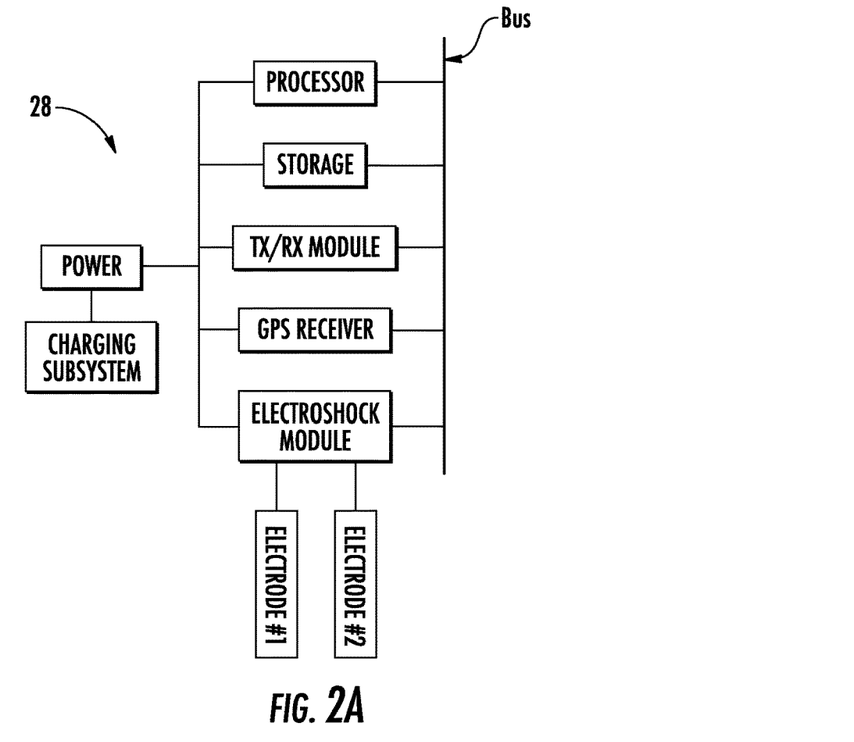
FIG. 2A is a diagram of an embodiment of a bracelet for controlling a prisoner or person subject to a restraining order according to the system and method described herein.
Figure 2B:
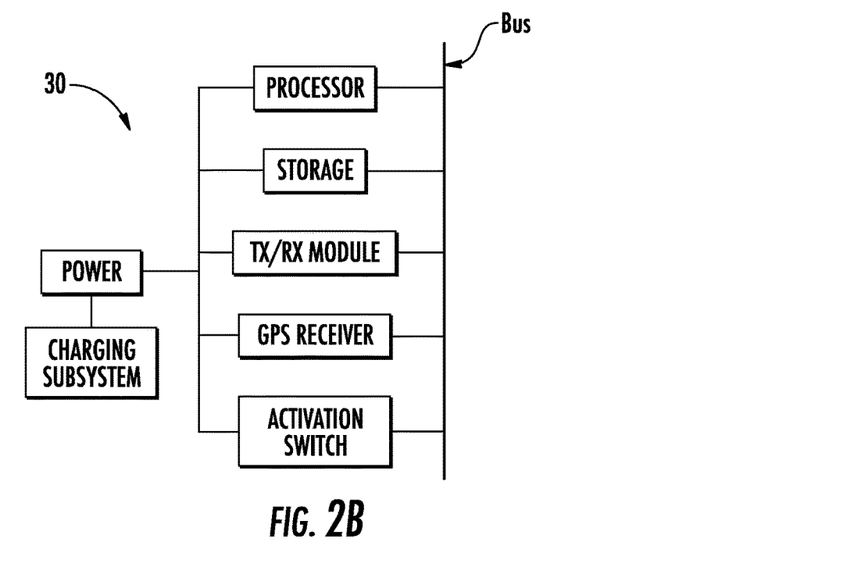
FIG. 2B is a diagram of an embodiment of a bracelet for a security officer or victim of domestic violence according to the system and method described herein.

Referring to FIG. 2A, in a first configured of the wearable device 10, the body 16 of the wearable device 10 contains a control module 28 comprising a processor, a storage, a transmitter/receiver module, a GPS receiver and an electroshock module, all interconnected via a system bus. The electroshock module includes a first electrode and a second electrode, which, as noted above, may be integrated into the first section 18 or the second section 20 of the wearable device 10. Furthermore, the electrodes 24 may appear on one or split across both sections 18, 20 of the body 16 of the wearable device 10. Referring to FIG. 2B, in a second configured of the wearable device, the body 16 of the wearable device 10 contains a control module 30 comprising a processor, a storage, a transmitter/receiver module, a GPS receiver and an activation switch 26, all interconnected via a system bus. In either configuration, components of the control module 28, 30 may be split across between the first section 18 and second section 20 of the body 16 of the wearable device 10.

A power source powers the components of the two configurations of the control module 28, 30 and includes enough capacity to operate for twenty-four hours, including operating the electroshock module at least twice for the first configuration. The power source may be recharged through a charging subsystem, which may include a motion-induced charging system, such as Faraday charging mechanism as well as conventional corded and wireless charging mechanisms, such as magnetic induction.

The body 16 of the wearable device 10 and/or control module 28, 30 may be sealed to prevent tampering and protect the control module 28, 30 from ingress of water or other fluids.

The storage may further include a unique identifier of the wearable device 10 and a unique identifier assigned to the subject 12 or user 14 of the wearable device 10.

Locking the double lock 22 activates the control module 28, 30 on the wearable device 10. Likewise, unlocking the double lock 22 disables the control module 28, 30, rendering the wearable device 10 inoperative.

In the second configuration, the activation switch is configured and arranged to cause the processor to transmit a signal to activate an electroshock module of another wearable device 10 within a predefined radius R of the user 14, such as 10 feet by way of example and not limitation. In some embodiments, activating the activation switch transmits the signal directly to the other wearable device 10. In other embodiments, the second configuration may also send a signal to the server, described further below.

Although the wearable device 10 is described as a handcuff to be worn on the wrist or forearm, it may also be on worn on other parts of the body, such as an ankle. The electric shocks emitted by the electroshock module of the first configuration are nonlethal, but strong enough to stun the subject, similar to a taser.

Figure 3A:
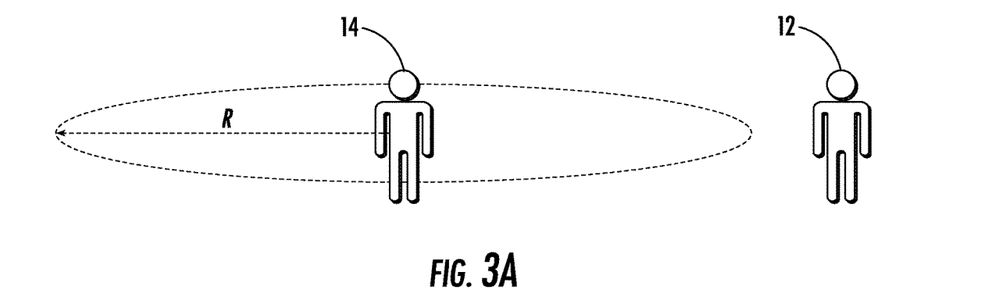
FIG. 3A is a diagram of a person wearing a prisoner control device who is outside of an active radius to a person wearing a security device according to the system and method described herein.
Figure 3B:
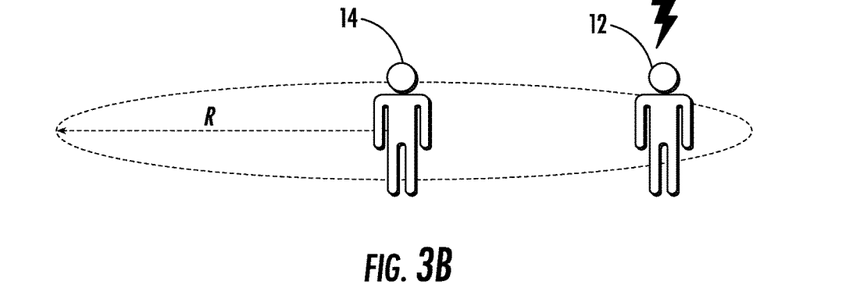
FIG. 3B is a diagram of a person wearing a prisoner control device who is inside of an active radius to a person wearing a security device according to the system and method described herein.

As shown in FIGS. 3A and 3B, a method of activating an electroshock module of a wearable device 10 is shown generally. A subject 14 wearing a wearable device 10 in a first configuration may approach a user 12 wearing a wearable device 10 in a second configuration. The user 14 may optionally warn the subject 12 away at this point. The user 14 may activate the activation switch. If the subject 14 continues to approach the user 12 and enters within a predefined radius R of the user 12, the subject's 14 electroshock module will then activate, shocking the subject 14 and incapacitating or subduing the subject 14. In other embodiments, the user 14 must activate the activation switch after the subject 12 enters the predefined radius R, in order to activate the subject's 12 electroshock module. In other embodiments, the subject's 12 electroshock module automatically activates when it detects it has entered the user's 14 predefined radius R without need for the user 14 to activate the activation switch.

In order to prevent inadvertent or unauthorized activations of electroshock modules, the control module 28, 30, with the processor, verifies the authenticity of an activation request received from a user's 14 wearable device or, as described further below, a server 32. In some embodiments, a lookup table containing wearable device identifiers of authorized wearable devices 10 or authorized users is maintained on the storage of the subject's 12 wearable device 10. In some embodiments, the request is verified by use of a secret code or PIN, which is matched against a code stored in a storage of the control module 28, 30. If the activation request is not verified as being authentic, the request, via the processor, is rejected. If the activation request is verified as being authentic, the control module 28, 30, via the processor, activates the electroshock module. The control module 28, 30, with the processor and transmitter/receiver module, communicates securely with the user's 14 wearable device 10 and/or server 32 to receive the device identifier and user identifier and/or secret code toe authenticate the activation request. Alternatively, these authentication credentials may be transmitted simultaneously with the activation request.

Figure 4A:
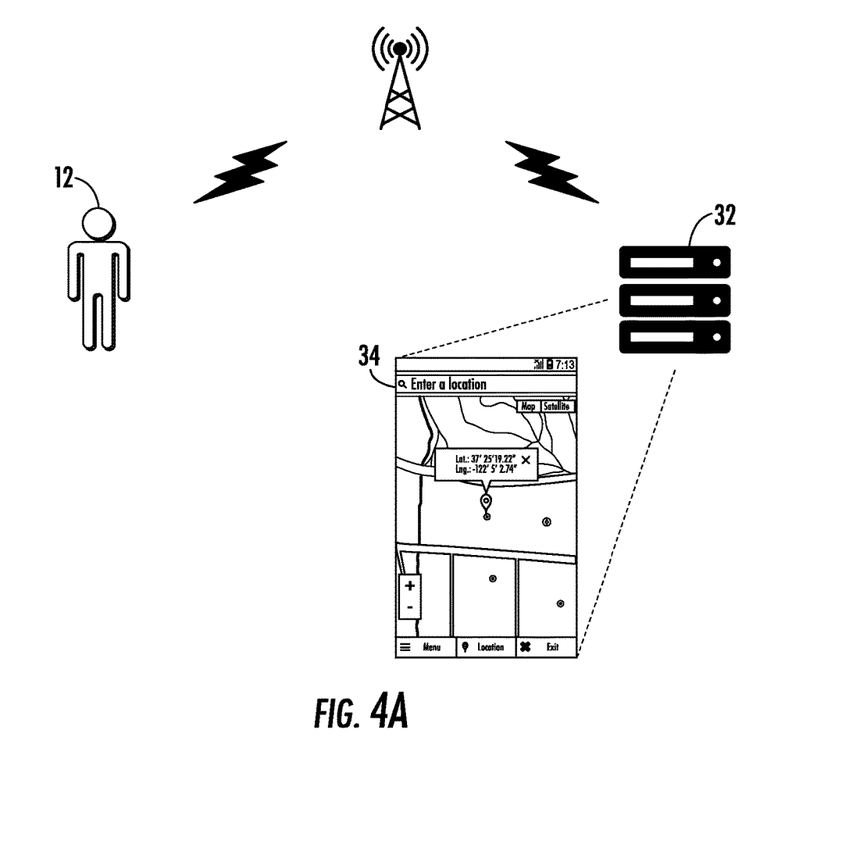
FIG. 4A is a diagram of an illustrative embodiment of a prisoner control system as described herein showing the geographic location information of a person wearing a device.
Figure 4B:
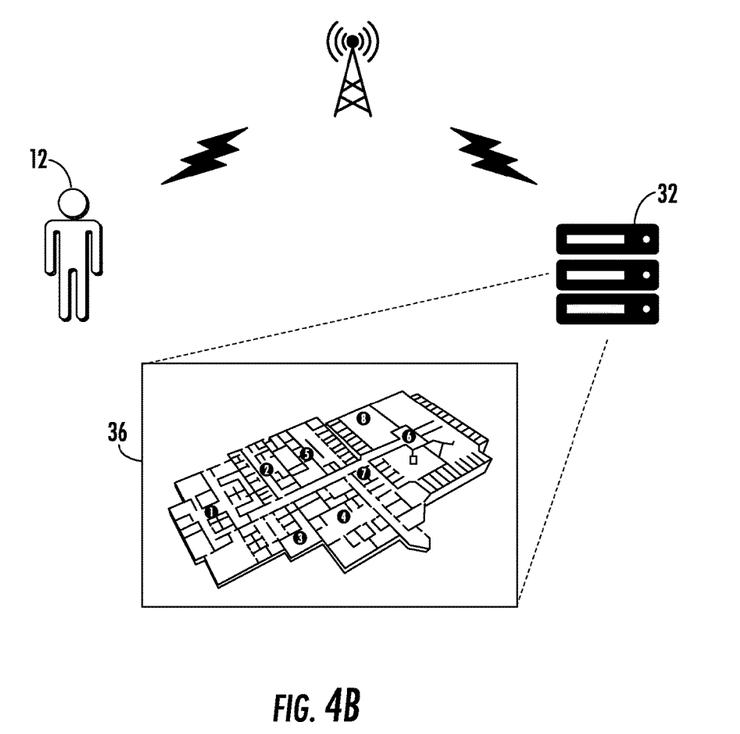
FIG. 4B is a diagram of an illustrative embodiment of a prisoner control system as described herein showing the geographic location information of a person wearing a device within a mapped environment, such as a prison.

As noted above, the system may further include a server 32 where remote tracking and activation of wearable devices 10 may be initiated from. The server 32 may include one or more computers, virtual machines, and/or cloud servers accessible through a web browsing software or proprietary application. The server 32 receives GPS coordinate information transmitted periodically from wearable devices 10 being tracked by the system. The system can overlay the GPS information over maps 34 (FIG. 4A) and floor plans 36 (FIG. 4B). From the server 32, users 14 may selectively activate individual, groups, grid position, or all electroshock modules of subjects 12 being tracked by the system. The system further logs past positions of all wearable devices 10 being tracked by the system for a preset time-period, such as 30 days. Other time periods may be used as desired. The system also stores the device identifier and user identifier for each wearable device 10 for easy cross-reference to pertinent information about the wearer of the wearable device, such as name, sex, height, weight, photograph, title, and, if applicable, incarceration information. The server 32 further logs the time, date and location information of all electroshock module activation, including the identity of the initiating device and the activated device. The server 32 maintains log of the remaining duration of the power source of each wearable device 10.

The server 32 may also issue commands to the wearable devices 10 being tracked by the system. Other requested actions may include requesting diagnostics, usage history, changing the authorized users and/or authorized devices, changing a secret code or PIN, updating firmware in the storage of the control module 28, 30, performing a system reset, and performing a system shutdown, for example and not by way of limitation.

As can be seen, the system and method described herein solves the problems of the prior art by providing a wearable device that includes an electroshock module, to be worn by and subject, and a wearable device, to be worn by a user, that permits the user to administer shocks to the subject if the subject enters a predefined radius of the user. This feature can enhance the safety of security officers and victims of domestic violence by deterring subjects from approaching. Those skilled in the art will appreciate that the conception, upon which this disclosure is based, may readily be utilized as a basis for designing other products without departing from the spirit and scope of the invention as defined by the appended claims. Therefore, the claims are not to be limited to the specific examples depicted herein. For example, the features of one example disclosed above can be used with the features of another example. Furthermore, various modifications and rearrangements of the parts may be made without departing from the spirit and scope of the underlying inventive concept. For example, the geometric configurations disclosed herein may be altered depending upon the application, as may the material selection for the components. Thus, the details of these components as set forth in the above-described examples, should not limit the scope of the claims.

What is claimed is:

1. A system, comprising:
   a first wearable device configured and arranged to be secured about an appendage of a first person, the first wearable device comprising a GPS receiver module, an electroshock module and wireless receiver;
   a second wearable device configured and arranged to be worn about an appendage of a second person, the second wearable comprising, a GPS receiver module, a transmitter and activation switch; and
   a server in wireless communication with the first wearable device and the second wearable device;
   wherein, if the first wearable device is within a predefined radius of the second wearable device, activation of the activation switch causes the transmitter to send a first signal directly to the wireless receiver to activate the electroshock module,
   wherein the activation of the activation switch further causes the transmitter to send a second signal to the server;
   wherein the electroshock module is configured to apply a stunning shock to the first person; and
   wherein, responsive to the second signal, the server is configured to authenticate an identity of the second wearable device having the activation switch and, responsive to the authenticating, enable the electroshock module.

2. The system of claim 1, wherein the first wearable device further comprises a tamper-proof locking mechanism.

3. The system of claim 1, wherein the first wearable device and second wearable device each further comprises a motion-induced charging system.

4. The system of claim 1, wherein:
   the server is configured and arranged to receive a GPS location from the first and second wearable devices and indicate the locations of the first and second wearable devices on at least one of a map or a floorplan.

5. The system of claim 4, wherein the server is further configured and arranged to transmit a signal to the first wearable device to activate the electroshock module.

6. The system of claim 4, wherein the server is configured and arranged to activate electroshock modules of a plurality of first wearable devices.

7. The system of claim 6, wherein the server is configured to activate electroshock modules by group, grid location or all wearable devices being tracked.

8. The system of claim 1,
   wherein the second wearable device is configured to authenticate the second person prior to the activation.

9. A system, comprising:
   a first wearable device configured and arranged to be secured about an appendage of a first person, the first wearable device comprising a GPS receiver module, an electroshock module and wireless receiver;
   a second wearable device configured and arranged to be worn about an appendage of a second person, the second wearable comprising, a GPS receiver module, a transmitter and activation switch; and
   a server in wireless communication with the first wearable device and the second wearable device, the server configured and arranged to receive a GPS location from the first and second wearable devices and indicate the locations of the first and second wearable device on at least one of a map or a floorplan, the server further configured to, responsive to the second signal, authenticate an identity of the second wearable device and, responsive to the authenticating, enable the electroshock module;

wherein, responsive to the enabling, the electroshock module of the first wearable device may be selectively activated by the second wearable device and the server.

10. The system of claim 9, wherein, if the first wearable device is within a predefined radius of a second wearable device, activation of the activation switch causes the transmitter to send a signal to the receiver to activate the electroshock module.

11. The system of claim 9, wherein the electroshock module of the first wearable device is activated automatically upon entering a predefined radius of the second wearable device.

12. The system of claim 9, wherein the first wearable device further comprises a tamper-proof locking mechanism.

13. The system of claim 9, wherein the first wearable device and second wearable device each further comprises a motion-induced charging system.

14. The system of claim 9, wherein the second wearable device is configured to authenticate the second person prior to the activation.

15. A system, comprising:
  a first wearable device configured and arranged to be secured about an appendage of a first person, the first wearable device comprising a GPS receiver module, an electroshock module and wireless receiver;
  a second wearable device configured and arranged to be worn about an appendage of a second person, the second wearable comprising, a GPS receiver module, a transmitter and activation switch; and
  a server in wireless communication with the first wearable device and the second wearable device, the server configured to authenticate an identity of the second wearable device, the server further configured and arranged to receive a GPS location from the first and second wearable devices and calculate a distance between the first and second wearable devices, the server further configured and arranged to transmit a signal to the first wearable device to activate the electroshock module of the first wearable device if the first wearable device is within a predefined radius of the second wearable device.

16. The system of claim 15, wherein the electroshock module of the first wearable device may be selectively activated by the second wearable device and server.

17. The system of claim 15, wherein the electroshock module of the first wearable device is activated automatically upon entering a predefined radius of the second wearable device.

18. The system of claim 15, wherein the first wearable device further comprises a tamper-proof locking mechanism.

19. The system of claim 15, wherein the first wearable device and second wearable device each further comprises a motion-induced charging system.

20. The system of claim 15, wherein the second wearable device is configured to authenticate the second person prior to the activation.

* * * * *